US00PP19153P3

(12) United States Plant Patent
Woolmore

(10) Patent No.: US PP19,153 P3
(45) Date of Patent: Aug. 26, 2008

(54) *LAURUS* PLANT NAMED 'PRIDE OF PROVENCE'

(50) Latin Name: *Laurus nobilis*
Varietal Denomination: Pride of Provence

(76) Inventor: Malcolm Woolmore, 82 Trig Road, Whenaupai, Auckland (NZ)

( * ) Notice: Subject to any disclaimer, the term of this patent is extended or adjusted under 35 U.S.C. 154(b) by 0 days.

(21) Appl. No.: 11/879,951

(22) Filed: Jul. 19, 2007

(65) Prior Publication Data

US 2008/0184409 P1 Jul. 31, 2008

(51) Int. Cl.
*A01H 5/00* (2006.01)

(52) U.S. Cl. ..... Plt./226

(58) Field of Classification Search ..... Plt./226, Plt./216

See application file for complete search history.

*Primary Examiner*—Kent L. Bell
*Assistant Examiner*—June Hwu

(57) ABSTRACT

A new cultivar of *Laurus* plant named 'Pride of Provence' that is characterized by a compact habit, a rounded shape and dark green leaves.

1 Drawing Sheet

Botanical classification: *Laurus nobilis*.
Variety denomination: 'Pride of Provence'.

BACKGROUND OF THE INVENTION

The present invention relates to a new and distinct variety of *Laurus* plant botanically known as *Laurus nobilis* and hereinafter referred to by the cultivar name 'Pride of Provence'.

The new cultivar is the product of a crossing of the female parent plant an unnamed *Laurus nobilis* plant (not patented) and the male parent plant an unnamed *Laurus nobilis* plant (not patented). 'Pride of Provence' was selected by the inventor as a single plant within the progeny of the stated cross in a cultivated area of Hamilton, New Zealand in 2001.

Asexual reproduction by tip cuttings of the new cultivar 'Pride of Provence' was first performed in 2001 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Laurus* cultivar 'Pride of Provence'.

1. *Laurus* 'Pride of Provence' exhibits a rounded shape.
2. *Laurus* 'Pride of Provence' exhibits a compact habit.
3. *Laurus* 'Pride of Provence' exhibits dark green leaves.

The closest comparison cultivars are the parent plants. The new cultivar 'Pride of Provence' is distinguishable from the unnamed female parent plant by the following characteristics:

1. 'Pride of Provence' has darker green leaves.
2. 'Pride of Provence' has a more compact habit.

The new cultivar 'Pride of Provence' is distinguishable from the unnamed male parent plant by the following characteristics:

1. 'Pride of Provence' has a more rounded plant shape.
2. 'Pride of Provence' has a more compact habit.

BRIEF DESCRIPTION OF THE DRAWING

The accompanying photograph illustrates the distinguishing traits of *Laurus* 'Pride of Provence'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Laurus* cultivar named 'Pride of Provence'. Data was collected in Auckland, New Zealand from 2 year old field grown plants. The time of year was Winter in the Southern Hemisphere and the average temperature range was 12 to 18 degrees Centigrade during the day and 4 to 11 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Pride of Provence' has not been tested under all possible conditions and phenotypic differences may be observed with variations in environmental, climatic, and cultural conditions, however, without any variance in genotype.

Botanical classification: *Laurus nobilis* 'Pride of Provence'.
Use: Ornamental perennial shrub.
Parentage:
*Female parent.*—An unnamed cultivar of *Laurus nobilis.*
*Male parent.*—An unnamed cultivar of *Laurus nobilis.*
Vigor moderate:
Growth rate: 0.3 meters per year.
Growth habit: Freely branching, compact habit.
Plant shape: Rounded.
Suitable container size: 2.0 liter container.
Height: Average 0.6 m in height.
Width: Average 0.5 m in width.
Hardiness: Tolerant to −12 degrees Centigrade.

Propagation: Tip cuttings.
Time to initiate roots: Approximately 90 days in the Summer and 135 days in the Winter.
Time to produce a rooted cutting: Approximately 135 days in the Summer and 180 days in the Winter.
Root system: Fine and fibrous.
Lateral branches:
*Quantity.*—Approximately 20.
*Length.*—Average 100 mm.
*Diameter.*—Average 3 mm.
*Internode length.*—12 mm.
*Shape: Rounded.*
*Color.*—143A when young turning to 152A when mature.
*Strength.*—Strong.
*Pubescence.*—Absent.
*Pinching.*—Yes.
Foliage:
*Texture.*—Leathery.
*Leaf arrangement.*—Alternate.
*Compound or single.*—Single.
*Quantity of leaves per lateral branch.*—7.
*Leaf shape.*—Elliptic.
*Leaf apex.*—Cuspidate.
*Leaf base.*—Rounded.
*Leaf length.*—Average 75 mm in length.
*Leaf width.*—Average 35 mm in width.
*Pubescence.*—Absent.
*Leaf margin.*—Entire.
*Young leaf color* (*upper surface*).—N189A.
*Young leaf color* (*lower surface*).—137B.
*Mature leaf color* (*upper surface*).—N189A.
*Mature leaf color* (*lower surface*).—137B.
*Vein color* (*both surfaces*).—N144A.
*Petiole length.*—10 mm.
*Petiole diameter.*—2 mm.
*Petiole color.*—N152B.
*Durability of foliage to stress.*—Moderate to high.
Flowers: Flowers have not been observed.
Disease and insect resistance: Plants of the new *Laurus* have not been observed for disease or insect resistance.

What is claimed is:

1. A new and distinct variety of *Laurus* plant named 'Pride of Provence' as described and illustrated.

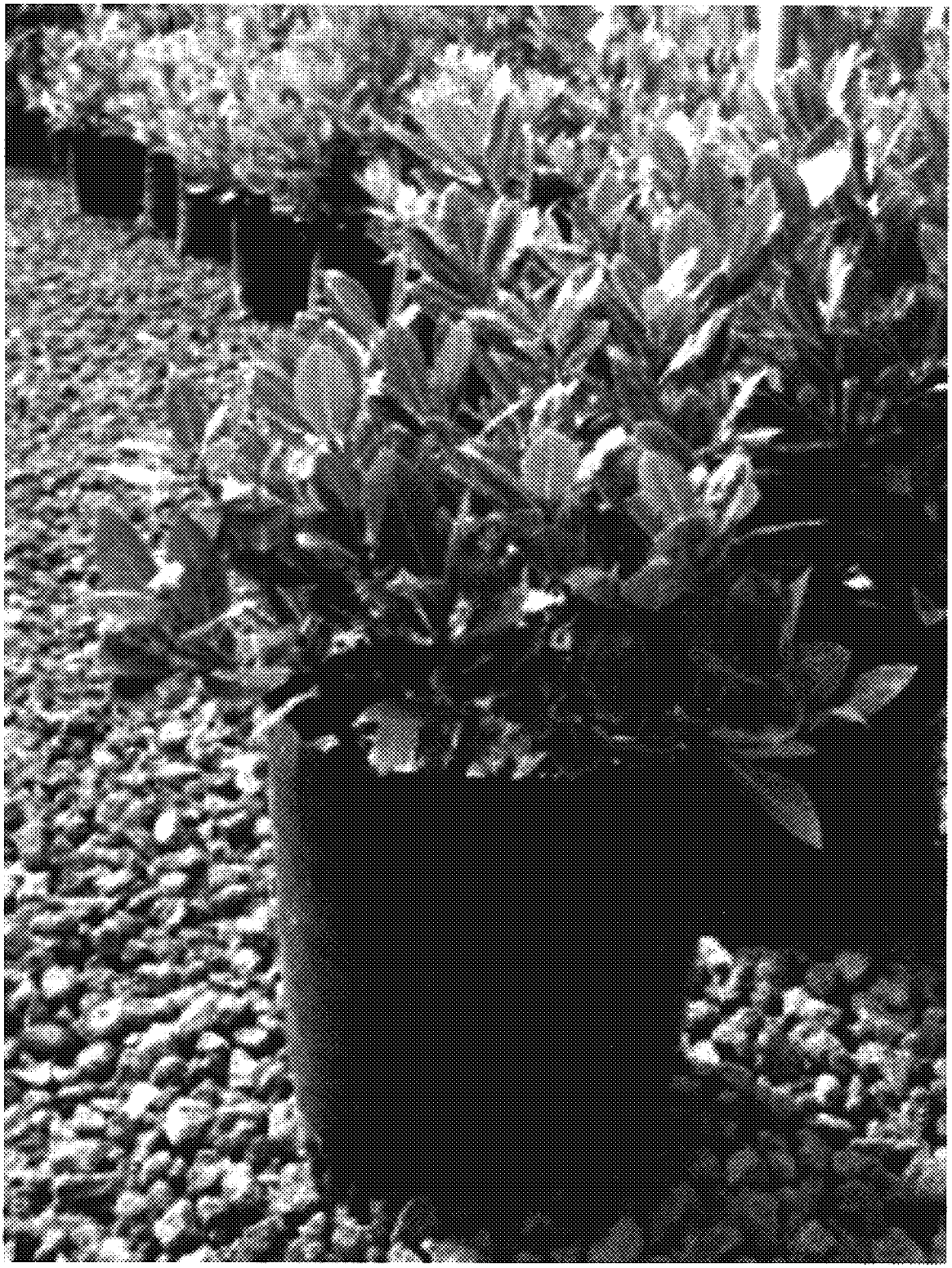

* * * * *